United States Patent [19]

Bays

[11] Patent Number: 5,769,093

[45] Date of Patent: Jun. 23, 1998

[54] METHOD OF RELIEVING SYNOVIAL FLUID PRESSURE

[75] Inventor: F. Barry Bays, Clearwater, Fla.

[73] Assignee: Xomed Surgical Products, Inc., Jacksonville, Fla.

[21] Appl. No.: 857,185

[22] Filed: May 15, 1997

Related U.S. Application Data

[60] Continuation of Ser. No. 594,076, Jan. 30, 1996, abandoned, which is a division of Ser. No. 353,483, Dec. 9, 1994, abandoned.

[51] Int. Cl.$^6$ .............................. A61B 19/00; A61M 5/00
[52] U.S. Cl. .................................. 128/898; 604/8; 604/9; 623/12
[58] Field of Search ................................. 604/8–10, 264, 604/19, 48, 49; 623/12; 137/855; 128/898

[56] References Cited

U.S. PATENT DOCUMENTS

| | | |
|---|---|---|
| 1,955,733 | 4/1934 | Bijur . |
| 2,969,066 | 1/1961 | Holter et al. . |
| 3,020,913 | 2/1962 | Heyer . |
| 3,111,125 | 11/1963 | Schulte . |
| 3,288,142 | 11/1966 | Hakim . |
| 3,298,372 | 1/1967 | Feinberg . |
| 3,595,240 | 7/1971 | Mishler . |
| 3,683,929 | 8/1972 | Holter . |
| 3,758,073 | 9/1973 | Schulte . |
| 3,788,327 | 1/1974 | Donowitz et al. . |
| 3,807,444 | 4/1974 | Fortune . |
| 3,827,439 | 8/1974 | Schulte et al. . |
| 3,871,380 | 3/1975 | Heros . |
| 3,910,283 | 10/1975 | Leveen . |
| 3,948,271 | 4/1976 | Akiyama . |
| 4,037,604 | 7/1977 | Newkirk . |
| 4,160,454 | 7/1979 | Foux . |
| 4,222,407 | 9/1980 | Ruschke . |
| 4,402,681 | 9/1983 | Haas et al. . |

(List continued on next page.)

FOREIGN PATENT DOCUMENTS

| | | |
|---|---|---|
| 2240026 | 4/1975 | France . |
| 2654937 | 11/1989 | France . |
| 88138 | 2/1896 | Germany . |
| 3343863 | 6/1985 | Germany . |
| 3639980 | 5/1988 | Germany . |
| 4001833A1 | 1/1990 | Germany . |
| 13268 | 1/1983 | Japan . |
| 4129569 | 4/1992 | Japan . |
| 189127 | 5/1923 | United Kingdom . |
| 1010067 | 11/1965 | United Kingdom . |
| 2069339 | 8/1981 | United Kingdom . |
| 2130890 | 11/1983 | United Kingdom . |

OTHER PUBLICATIONS

"An In Vivo Study of Intra–Capsular Pressure in Patients With Total Hip Replacement Complicated By Osteolysis," 3rd Annual Mtg., Assoc. for Arthritic Hip & Knee Surgery, Nov. 12–14, 1993, Dallas, Texas.

"Analysis of Cementless Disease; An In Vitro And In Vivo Study" by W. L. Lanzer et al, ABJS Meeting, Williamsburg, Va., Apr. 27–30, 1992, (Two Pages).

(List continued on next page.)

Primary Examiner—Mark O. Polutta

[57] ABSTRACT

A device for relieving synovial fluid pressure in a capsule surrounding a body joint includes a valve for placement in the capsule surrounding the joint for regulating passage of synovial fluid from the capsule. The valve can include a valve housing defining a passage between an interior and exterior of the capsule and a valve member disposed within the valve housing for regulating synovial fluid pressure within the capsule by permitting synovial fluid to drain from the capsule when a predetermined synovial fluid pressure is exceeded. The valve housing can be secured to the capsule with inlet and outlet flanges disposed at opposite ends of the housing and, additionally, by use of openings formed in the outlet flange to allow passage of sutures and to promote integral tissue fixation over time.

5 Claims, 2 Drawing Sheets

U.S. PATENT DOCUMENTS

| | | |
|---|---|---|
| 4,413,985 | 11/1983 | Wellner et al. . |
| 4,443,214 | 4/1984 | Marion . |
| 4,465,062 | 8/1984 | Versaggi et al. . |
| 4,552,553 | 11/1985 | Schulte et al. . |
| 4,568,337 | 2/1986 | Treharne, III et al. . |
| 4,636,194 | 1/1987 | Schulte et al. . |
| 4,676,772 | 6/1987 | Hooven . |
| 4,679,546 | 7/1987 | van Doorn et al. . |
| 4,714,458 | 12/1987 | Hooven . |
| 4,744,792 | 5/1988 | Sander et al. . |
| 4,772,261 | 9/1988 | Von Hoff et al. . |
| 4,776,839 | 10/1988 | Doumenis . |
| 4,822,368 | 4/1989 | Collier . |
| 4,883,456 | 11/1989 | Holter . |
| 4,886,488 | 12/1989 | White . |
| 4,964,850 | 10/1990 | Bouton et al. . |
| 5,026,378 | 6/1991 | Goldsmith, III . |
| 5,069,663 | 12/1991 | Sussman . |
| 5,120,312 | 6/1992 | Wigness et al. . |
| 5,122,114 | 6/1992 | Miller et al. . |
| 5,163,924 | 11/1992 | Beverly . |
| 5,176,627 | 1/1993 | Watson . |
| 5,178,623 | 1/1993 | Cinberg et al. . |
| 5,261,448 | 11/1993 | Furuya et al. . |
| 5,300,020 | 4/1994 | L'Esperance, Jr. . |
| 5,334,137 | 8/1994 | Freeman . |
| 5,378,228 | 1/1995 | Schmalzried et al. . |

OTHER PUBLICATIONS

"In Vitro Human Bone Cell Proliferation; The Effects of Implant Particulates and Elevated Temperature" by W.L.Lanzer et al,37th Annual Meeting,Orthopaedic Research Society,Mar. 4–7, 1991,Anaheim,California.

"Intra–Capsular Pressure In Patients With Total Hip Replacement Complicated By Osteolysis: An In Vivo Study", W.L.Lanzer et al, 20th Annual Meeting of the Society for Biomaterials, Apr. 5–9, 1994, Boston, Massachusetts.

"MRNA In–Situ Hybridization of Human Bone Cells: An In Vitro and Ex Vivo Study of Implant Particulates" W. L. Lanzer et al, Implant Retrieval Symposium of the Society for Biomaterials, Sep. 17–20, 1992 St. Charles, Illinois.

"The Effects of Implant Wear Debris On Human Bone Cell Proliferation in Vitro", W. L. Lanzer et al The 16th Annual Meeting of the Society of Biomaterials.

"An In Vitro and In Vivo Analysis of Cementless Disease", W. L. Lanzer et al, Second Annual Meeting, Association for Arthritic Hip and Knee Surgery, Nov. 13–15, 1992 Dallas, Texas.

Periprosthetic Bone Loss In Total Hip Replacement: The Role of High Density Polyethylene (HDP) Wear Debris and the Concept of the Effect Joint Space, T. P. Schmalzried and W. H. Harris, 38th Annual Meeting, Orthopaedic Research Society, Feb. 17–20, 1992, Washington, D. C.

"Particulate Wear Debris in Patients With Total Hip Replacement Complicated by Osteolysis: An In Vitro and In Vivo Study," 57th Annual Meeting, Western Orthopaedic Association, Aug. 29–Sep. 2, 1993 Seattle, Washington.

"Arthrography After Total Hip Arthroplasty: A Modified Technique Used in the Diagnosis of Pain," by by Ronald W. Hendrix, M.D. et al, Radiology, vol. 148, No. 3, Sep. 1983, pp. 647–652.

"Mechanism and Clinical Significance of Wear Debris–Induced Osteolysis," Harlan C. Amstutz, M.D. et al Clinical Orthopaedics and Related Research, No. 276, Mar. 1992, pp. 7–11.

"Localised Endosteal Bone Lysis in Relation to the Femoral Components of Cemented Total Hip Arthroplasties", by P. P. Anthony et al, Journal of Bone and Joint Surgery, 1990, pp. 971–979.

"Aseptic Loosening in Total Hip Arthroplasty Secondary to Osteolysis Induced by Wear Debris From Titanium–Alloy Modular Femoral Heads" by Adolph V. Lombardi, Jr., M.D., The Journal of Bone and Joint Surgery, vol. 71–A, No. 9, Oct. 1989, pp. 1337–1342.

"A Rat Model of Resorption of Bone at the Cement–Bone Interface in the Presence of Polyethylene Wear Particles" by D. W. Howie, et al, The Journal of Bone and Joint Surgery, vol. 70–A, No. 2, Feb. 1988, pp. 257–262.

"Etiology of Osteolysis Around Porous–Coated Cementless Total Hip Arthroplasties," by Murali Jasty, M.D. et al., Clinical Orthopaedics and Related Research, No. 308, pp. 111–126.

"The Progression of Femoral Cortical Osteolysis in Association With Total Hip Arthroplasty Without Cement," by Michael Tanzer, M.D. et al., The Journal of Bone and Joint Surgery, pp. 404–410.

"Intracapsular Pressure Monitoring During Arthrographic Evaluation of Painful Hip Prostheses" by Robert Robert O. Cone, et al, AJR 141, Nov. 1983, pp. 885–889.

"Bone Lysis in Well–Fixed Cemented Femoral Components," by W. J. Maloney et al, Journal of Bone and and Joint Surgery, 1990, pp. 966–970.

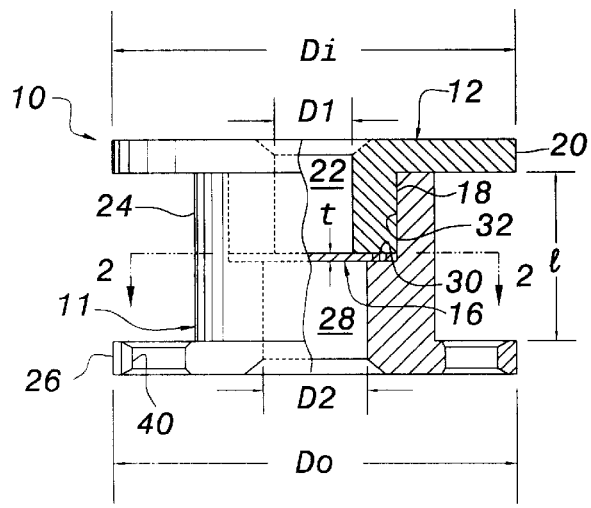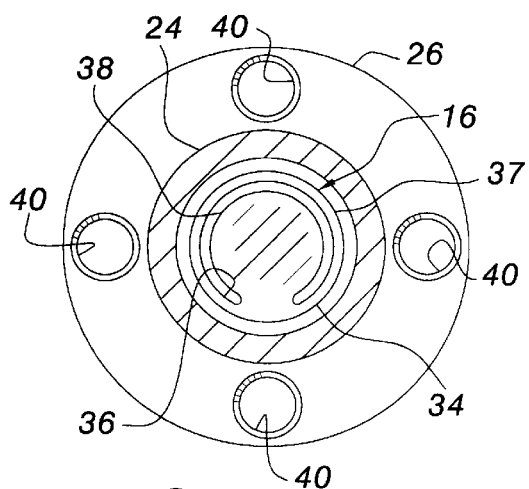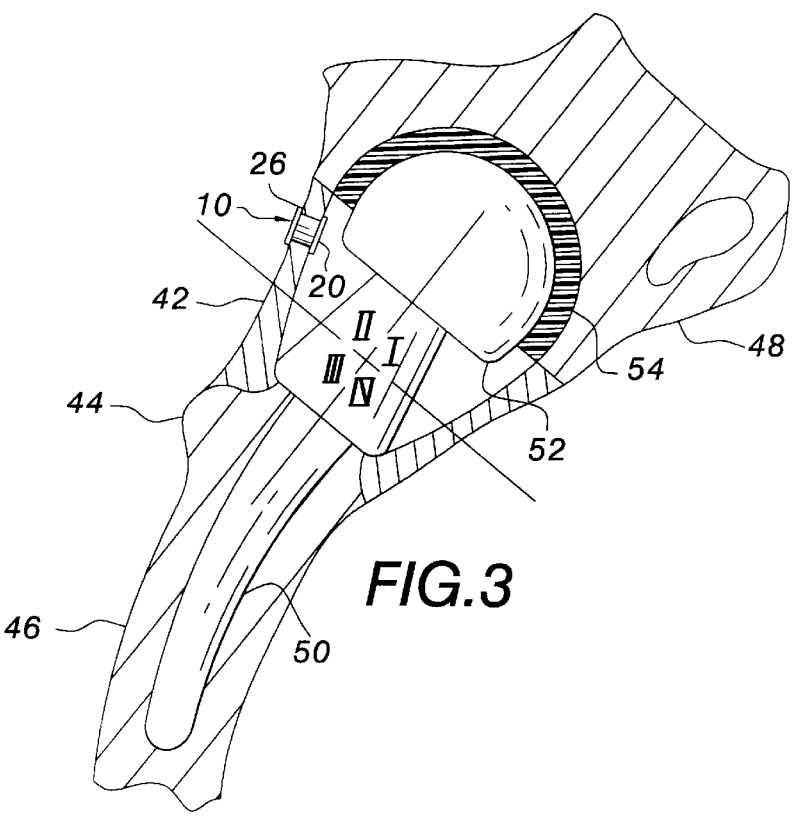

METHOD OF RELIEVING SYNOVIAL FLUID PRESSURE

This application is a continuation of patent application Ser. No. 08/594,076, filed Jan. 30, 1996, now abandoned which is a division of patent application Ser. No. 08/353,483, abandoned filed Dec. 9, 1994.

BACKGROUND OF THE INVENTION

1. Field of the Invention

The present invention relates to a device and method for reducing osteolytic complications following joint replacement surgery and, more particularly, to a valve assembly implantable in the capsular tissue surrounding a hip joint for preventing osteolysis in the femur and acetabular bones following total hip replacement surgery.

2. Discussion of the Prior Art

Hip replacement is most often performed on older patients whose joints have become stiff and painful as a result of osteoarthritis. It may also be needed if rheumatoid arthritis has spread to the hip joint or if the top end of the femur is badly fractured. The operation typically involves making a number of is incisions around the hip and pushing aside or cutting the surrounding muscle tissue to gain access to the hip joint. The 11 fibrous capsule surrounding the joint is then cut and, in some procedures, the trochanter near the top of the femur detached, so that the hip joint can be dislocated to separate the femur and the pelvis. The femoral head or ball at the top of the femur is then cut away and a shaft is cut into the femur for accommodating a metal trunnion carrying a ball at one end to serve as a replacement for the femoral head. The pelvis is also surgically modified to enlarge the acetabular space to accommodate a plastic or metal cup-shaped socket or liner. The trunnion and liner components are held in place with or without cement depending on the particular design of the prosthesis. The ball is then placed in the socket or liner and the trochanter reattached to the femur. Finally, the fibrous capsule and muscle tissue are replaced and repaired and any incisions closed.

A problem associated with hip replacement surgery is that resorption of periprosthetic bone can cause loosening of the prosthetic ball and socket thereby necessitating revision surgery. See, e.g., T. P. Schmalzried et al, "Periprosthetic Bone Loss in Total Hip Replacement: The Role of High Density Polyethylene (HDP) Wear Debris and the Concept of the Effect Joint Space," Orthopaedic Research Society, 38th Annual Meeting, February 17–20, 1992. When the periprosthetic bone loss appears localized or "scalloped," it is called "osteolysis," and is distinguished from those cases where the bone loss is more evenly distributed around the prostheses. In cemented protheses, the discovery of particulate PMMA in local areas of lysis led some investigators to conclude that a "cement disease" was the cause of the resorption; however, continuing reports of lysis in connection with cementless fixation of the ball and liner components indicates that the problem is not limited to cemented prostheses.

Recently, investigators have postulated that a non-phasic relationship between peak intracapsular fluid pressure and joint loading due to joint position and muscle activity may drive joint fluid (i.e., synovial fluid) and particulate debris through the joint space creating an intra-articular periprosthetic circulation leading to progressive bone resorption.

SUMMARY OF THE INVENTION

Accordingly, it is a primary object of the present invention to regulate synovial fluid pressure in a fibrous capsule surrounding a joint by implanting a valve in the capsular tissue.

It is another object of the present invention to reduce the occurrence of osteolysis following total hip replacement and other joint replacement surgery by regulating synovial fluid pressure in the fibrous capsule surrounding the joint.

A further object of the present invention is to implant a valve in the fibrous capsule surrounding a joint during open joint replacement or revision surgery to regulate synovial fluid pressure within the capsule.

Still another object of the present invention is to arthroscopically implant a valve in the fibrous capsule surrounding a joint to regulate synovial fluid pressure within the capsule.

The present invention is generally characterized in a device for relieving synovial fluid pressure in a body joint surrounded by a capsule including a valve housing for placement in the capsule, the valve housing defining a passage between an interior and an exterior of the capsule, and a valve member disposed within the valve housing for regulating synovial fluid pressure within the capsule by permitting synovial fluid to drain from the capsule when a predetermined synovial fluid pressure is exceeded. The valve housing can be secured to the capsule with inlet and outlet flanges disposed at opposite ends of the housing and, additionally, by use of openings formed in the outlet flange to allow passage of sutures and to promote integral tissue fixation over time.

Another aspect of the present invention is generally characterized in a valve assembly for relieving synovial fluid pressure in a capsule surrounding a joint including an outlet housing having a tubular outlet shaft defining an outlet passage and an outlet flange extending from a proximal end of the tubular outlet shaft, an inlet housing having a tubular inlet shaft defining an inlet passage and an inlet flange extending from a distal end of the tubular inlet shaft, and a disk disposed between the inlet and outlet housings and having an arcuate slot formed part way around the disk to form a rim and a flap depending from the rim between the inlet and outlet passages for regulating drainage of synovial fluid from the capsule.

Yet another aspect of the present invention is generally characterized in a method of relieving synovial fluid pressure in a capsule surrounding a joint including the steps of creating an opening in the capsule, implanting a valve in the opening to create a passage from an interior of the capsule to an exterior of the capsule, securing the valve to the capsule to prevent extrusion of the valve and regulating the synovial fluid pressure within the capsule by using the valve to drain synovial fluid from the capsule through the passage when a predetermined synovial fluid pressure is exceeded. The valve can be implanted during open joint replacement or revision surgery or by arthroscopic methods following joint replacement or revision surgery.

Other objects and advantages of the present invention will become apparent from the following description of the preferred embodiments taken in conjunction with the accompanying drawings, wherein like parts in each of the several figures are identified by the same reference characters.

BRIEF DESCRIPTION OF THE DRAWINGS

FIG. 1 is a side view, partly in section, of a valve assembly according to the present invention.

FIG. 2 is a cross-sectional view of the valve assembly of FIG. 1 taken through line 2—2.

FIG. 3 is an illustration of a valve assembly according to the present invention implanted within a fibrous capsule surrounding an artificial hip joint.

DESCRIPTION OF THE PREFERRED EMBODIMENTS

Figure 4:
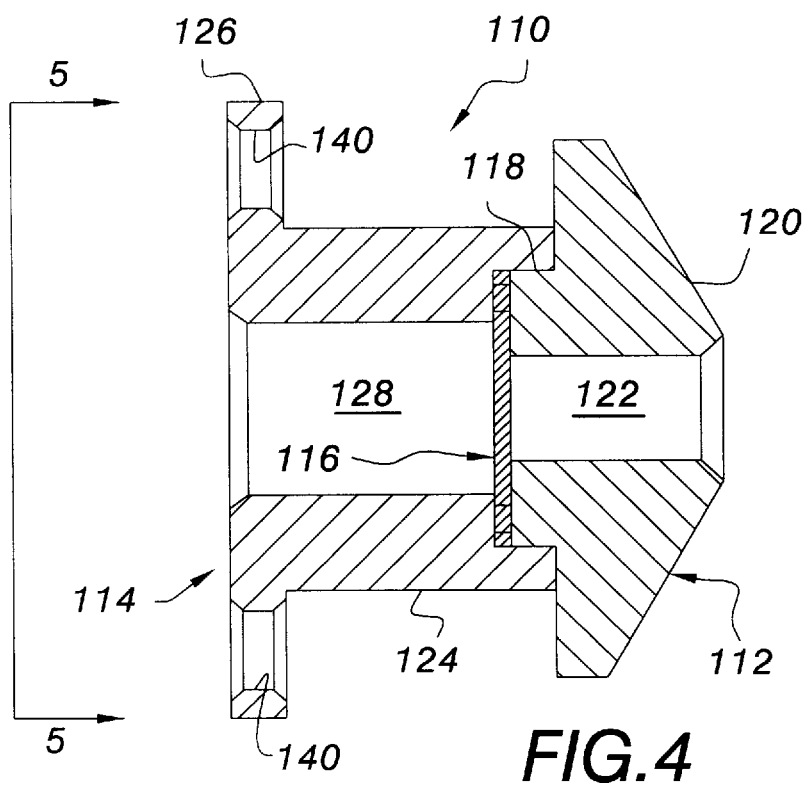
FIG. 4 is a cross-sectional view of a modified valve assembly according to the present invention.

The valve assembly of the present invention is described hereinafter as a device for regulating intracapsular synovial fluid pressure within a fibrous capsule surrounding a joint in the body. While the device of the present invention can be implanted in any of the fibrous capsules surrounding joints at various locations-in the body to reduce fluid pressure therein, the device is described hereinafter for preventing osteolytic complications following joint replacement surgery of the hip.

The device of the present invention, as illustrated in FIG. 1, is embodied in a valve assembly 10 forming a one-way valve. The valve assembly 10 includes a tubular valve housing 11 having any desired configuration in cross-section and a valve member 16 disposed within the tubular valve housing. The valve housing 11 defines a passage with a valve seat formed by an inlet housing or cap 12 and an outlet housing or cap 14. Inlet housing 12 includes a tubular shaft 18 and a round inlet flange 20 at a distal end of the tubular shaft. Tubular shaft 18 is generally cylindrical and defines an inlet passage 22. Outlet housing 14 includes a tubular shaft 24 and an annular outlet flange 26 at a proximal end of the tubular shaft 24. Tubular shaft 24 is generally cylindrical and defines an outlet passage 28 extending from the proximal end of the tubular shaft to a radial step or shoulder 30 at the bottom of a cylindrical recess 32 formed in the distal end of the tubular shaft 24.

As best seen in FIG. 2, valve member 16 includes a circular shim or disk 34 with an arcuate slot or cut-out 36 extending part way (e.g., about 282°) around the disk to define an annular rim 37 and a cantilevered valve member or flap 38 depending from an inner edge of the rim. Rim 37 of the disk is mounted on shoulder 30 with the valve flap 38 positioned over the outlet passage 28. Tubular shaft 18 of inlet housing 12 is telescopically fitted within the recess 32 of outlet housing 14 to hold the valve member 16 in place. Inlet passage 22 is somewhat smaller in diameter than outlet passage 28 so that the proximal end of tubular shaft 18 forms a shoulder defining a valve seat overlapping a peripheral edge of the valve flap 38.

A plurality of holes 40 are formed in the outlet flange 26 and are suitably sized (e.g., about 0.05 inches in diameter) for accommodating passage of suture material and to facilitate integral tissue fixation over time. Inlet and outlet flange diameters $D_i$ and $D_o$ will vary depending on the size and location of the capsule and the position of the valve assembly within the capsule. The flange diameters are chosen so that when the flanges are located on opposite sides of the capsular tissue the flanges will resist extrusion of the valve assembly from the capsular tissue under normal joint movement. The spacing Q between inlet and outlet flanges 20 and 26 will vary depending upon the thickness of the capsular tissue where the valve assembly is to be implanted.

The one-way valve is designed to open when intracapsular synovial fluid pressure on the inlet side of the valve exceeds normal levels and to close when the pressure drops back to normal. Opening of the valve occurs when pressure on the inlet side of the valve flap 38 causes the flap to deflect or be lifted away from the valve seat formed by the end of the tubular inlet shaft 18. The deflected flap 38 is elastically pivoted into outlet passage 28 to define a narrow crescent-shaped aperture within the outlet passage for permitting synovial fluid to seep out of the capsule into the surrounding tissue. When normal intracapsular synovial fluid pressure levels are achieved, the pressure acting on the valve flap 38 is reduced and the elastic properties of the valve material causes the flap to be reseated against the tubular shaft 18. Lifting pressure, that is, the pressure at which the valve flap 38 deflects to allow passage of synovial fluid and particulates through the valve assembly 10, depends primarily on the valve material chosen, the diameter $D_1$ of the inlet passage 22, the diameter $D_2$ of the outlet passage 28, the circumferential length of the arcuate-slot 36 and the thickness t of the valve member 16.

In a preferred embodiment, the inlet and outlet flange diameters $D_i$ and $D_o$ vary from about 0.1 to about 0.5 inches to prevent extrusion of the valve assembly from the capsule surrounding a hip joint and the spacing l between inlet and outlet flanges 20 and 26 will similarly vary from about 0.1 to about 0.5 inches depending upon the position of the valve assembly in the capsule and the thickness of the capsular tissue at that position. For an artificial hip joint, intracapsular synovial fluid pressure ranges from about 0 mm Hg at a resting anatomical position to about 700 mm Hg during activity and due to the increased pressure caused by component debris within the synovial fluid. About 7 to 10 mm Hg is considered normal. In accordance with one aspect of the present invention, therefore, the valve flap 38 is designed to open or lift when intracapsular pressure is elevated to about 15 to 25 mm Hg and to close when the pressure drops to normal levels in the range of about 7 to 10 mm Hg. These requirements can be met by a stainless steel valve assembly 10 having an inlet passage diameter $D_1$ of about 0.03 to about 0.04 inches, an outlet passage diameter $D_2$ of about 0.08 to about 0.09 inches, a circumferential slot length of about 280° to about 285°, and a disk thickness t ranging from about 0.001 to about 0.004 inches. A 0.035 inch diameter inlet passage coupled with a 0.004 inch thick stainless steel disk and a 282° slot has been found to provide a reasonable combination of lifting pressure and reseating performance over time when subjected to intracapsular pressures approximating those found in a hip joint.

The valve components can be made of any suitable medically-acceptable metal or plastic materials capable of being sterilized by use of conventional equipment employing electron-beam, ethylene oxide or other methods, but are preferably made of stainless steel. Examples of the types of stainless steel that can be used include ASTM F-138 316LVM stainless steel for the inlet and outlet housings 12 and 14, and Type 316 stainless steel for the valve 16.

Valve member 16 can be machined using a photo-etch method or any other suitable manufacturing process; and, as mentioned previously, the valve rim 37 is configured to rest on the shoulder 30 at the bottom of the recess 32 formed in the outlet housing 14. Valve flap 38 is positioned over the outlet passage 28 and is dimensioned to fit within the outlet passage when deflected. With the disk 34 supported on shoulder 30, the tubular shaft 18 of inlet housing 12 is snugly fitted within recess 32 and is fixed in place, for example by shrink fitting methods using liquid nitrogen or dry ice to contract the inlet housing 12 so that it can be located within the outlet housing 14 when contracted to create an interference fit after expanding to its normal dimensions. The tubular shaft 18 holds the valve member 16 in place and serves as a valve seat for the valve flap 38.

The valve assembly 10 can be delivered alone or placed in a pouch with the artificial joint components for being implanted during open surgery, or the valve assembly can be provided separately for being implanted arthroscopically after joint replacement or revision surgery.

Implantation of the one-way valve as part of open hip replacement surgery will now be described with reference to FIG. 3. As described previously, total hip replacement surgery typically involves making incisions in the hip at a number of locations to expose the fibrous capsule 42 surrounding the joint. The trochanter 44 near the top of the femur 46 is then detached so that the capsule 42 can be opened and the hip joint dislocated to separate the femur 46 from the pelvis 48. The existing femoral head is cut away, and a conventional metal trunnion 50 with a conventional replacement ball 52 is inserted into the femur 46. A reamer is used to enlarge the acetabular space in the pelvis 48 so that a conventional plastic or metal- socket 54 can be fitted in the normal manner. The ball 52 is placed in the socket 54, and the trochanter 44 is reattached using wires. At this point, the fibrous capsule 42 is repositioned around the prosthetic joint and repaired. The preceding operative steps are typical of a conventional total hip replacement surgery; and, accordingly, no attempt is made herein to provide a detailed description of such surgery.

In accordance with the present invention, a small incision is made in the capsule 42 prior to repairing the tissue surrounding the joint, and the valve assembly 10 is removed from a sterile delivery container or package, preferably by positioning jaws of a forceps around the outlet flange 26 and grasping the flange with the jaws. Inlet flange 20 of the valve assembly 10 is then inserted through the incision until the outlet flange 26 abuts an exterior surface of the capsule 42. The valve assembly 10 is thus positioned in the capsular tissue with opposed flanges 20 and 26 on opposite sides of the capsule 42 to resist extrusion of the valve from the capsular tissue.

For purposes of illustration, the hip joint has been divided into four quadrants I, II, III and IV, with the valve being shown implanted at a lateral position within the upper quadrant II between anterior and posterior areas of the quadrant. It will be appreciated, however, that the valve of the present invention can be implanted at any anterior, posterior or lateral location within one of the quadrants.

With the valve assembly 10 positioned within the capsular tissue, one or two absorbable sutures are passed through the outlet flange holes 40 and into the surrounding capsular tissue to secure the valve to the capsular tissue and to prevent migration or extrusion of the valve for a short period of a few weeks following surgery. Over time, tissue will infiltrate the outlet flange holes 40 making the valve assembly a permanent implant.

Once installed, the valve will operate to maintain intracapsular fluid pressure within a normal range (e.g., about 7 to 10 mm Hg in the hip joint). When intracapsular pressure is elevated to a point where the synovial fluid is driven through the joint creating a potentially harmful intra-articular current (e.g., at about 15 to 25 mm Hg), the valve flap 38 is deflected or lifted a small amount (e.g., about 0.001 to 0.002 inches) to discharge a small volume of synovial fluid and suspended particles (on the order of 1 to 10 μm in size) into the tissue surrounding the hip capsule 42. The synovial fluid drained from the capsule is absorbed by the surrounding tissue and any debris particles suspended in the fluid will remain in the surrounding tissue without complication. Pressure within the capsule is thus gradually reduced (e.g., over a period of hours), and the flap 38 will eventually reseat against tubular shaft 18 when a normal joint pressure is achieved.

Figure 5:
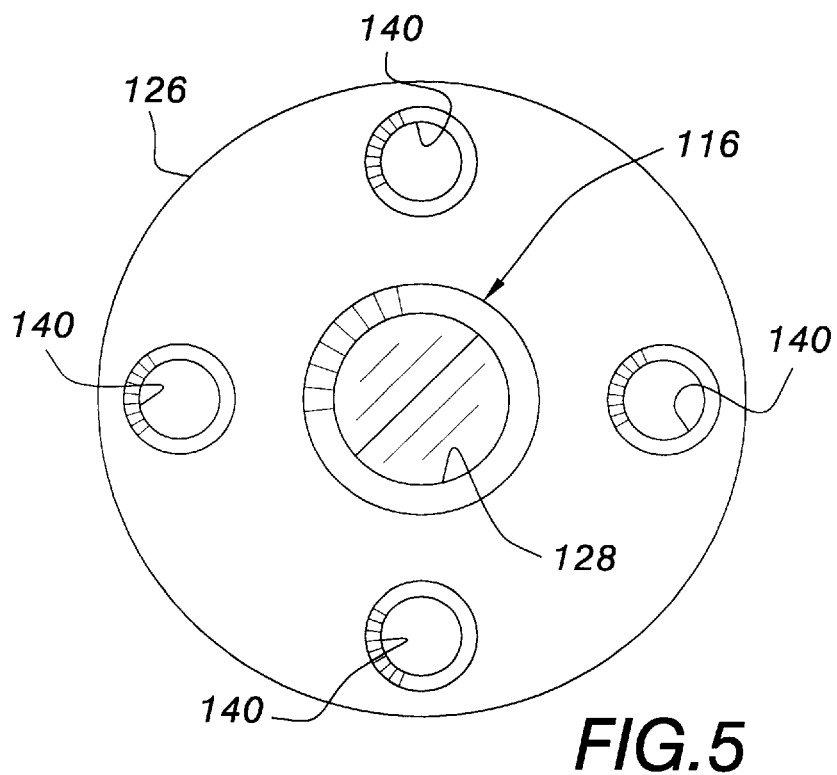
FIG. 5 is a front view of the valve assembly of FIG. 4 taken along line 5—5.

The modified valve assembly 110 shown in FIGS. 4 and 5 is similar to valve assembly 10 but with a frustoconically shaped inlet flange 120 and an oversized outlet flange 126. The modified valve assembly 110 is particularly well suited for being arthroscopically implanted because of the external shape of the inlet flange 120 which facilitates easy insertion through a small incision. The outlet flange 126 is larger than the inlet flange 120 to prevent the valve assembly from slipping, extruding or being forced into the capsular space which could impede the motion of the hip and require unnecessary surgery to remove. The large outlet flange also clearly identifies the exterior or outlet side of the valve assembly.

Any of the valve assemblies described herein can be implanted during open joint replacement or revision surgery or by arthroscopic approach following joint replacement or revision surgery. An exemplary arthroscopic procedure for implanting a valve in a capsule surrounding an artificial hip joint proceeds as follows. The patient is positioned on his side with a leg held in traction so that the fat surrounding the hip slides away from the operative site. Alternatively, a direct anterior approach is combined with the lateral approach by tilting the patient slightly onto the patient's back. Portals are positioned around the trochanter (indicated at 44 in FIG. 3), and cannulae are used to maintain and dilate the portals. A capsulotomy is made under one of the portals to create an incision in the capsule 42 through which a valve, such as valve assembly 110, is inserted. The valve inlet flange 120 is advanced into the incision in the capsular wall until the valve outlet flange 126 abuts the capsule. The valve assembly 110 is then sutured to the surrounding capsular tissue using appropriate arthroscopic instruments and techniques and will become incorporated into the tissue over time. Operation of the arthroscopically implanted valve assembly is as previously described.

From the above, it will be appreciated that in accordance with the present invention, a valve can be used to regulate the synovial fluid pressure within the fibrous capsule surrounding a joint and to extract small debris particles from the joint thereby reducing or preventing osteolytic complications following joint replacement or revision surgery. It will also be appreciated that the valve assembly and method of the present invention allows continuous drainage of synovial fluid from a joint without the need of having access to the joint. The valve assembly can be implanted in the capsular tissue surrounding the joint during open joint replacement or revision surgery or by minimally invasive or arthroscopic procedures performed sometime after joint replacement or revision surgery has been performed.

The valve assemblies shown and described herein are particularly advantageous when used for regulating intracapsular synovial fluid pressure. In accordance with the method of the present invention, however, other valves, including valves having tubular housings resembling conventional drain or vent tubes but with valve members placed within the tubes, can be used. For example, the housing of the valve assembly could resemble a Donaldson-type drain tube or a T-type ventilation tube, but with valve members disposed within the tubes. The valves can use single flaps as shown, multiple flaps in parallel and/or series, or any other type of valve member including duckbill, ball or membrane-type valves.

The valve assembly of the present invention can be positioned in the capsular tissue surrounding a joint at any anterior, posterior or lateral location and at any position along the length of the capsule. In the case of hip joints, the valve assembly can be positioned at any anterior, posterior or lateral location within one of the quadrants shown in FIG. 3. Under certain circumstances it may also be desirable to insert more than one valve at various locations around a capsule surrounding a joint.

The material specifications and dimensions of the valve assembly will vary according to the intended use and, as such, it will be appreciated that the particular materials and dimensions listed herein are merely exemplary and not meant to be limiting. The surfaces of the valve and the inlet and outlet passages of the valve assembly can also be treated using conventional biocompatible coatings that will inhibit the growth of tissue within the passages or on the valve.

The appropriate amount of deflection of the valve flap will depend on the volume of fluid to be extracted, the period of time over which the extraction is to occur and the anticipated size of any debris or particles suspended in the synovial fluid.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A method of relieving synovial fluid pressure in a capsule surrounding a joint comprising the steps of creating an opening in the capsule;

implanting a valve in the opening to create a passage from an interior of the capsule to an exterior of the capsule;

securing the valve to the capsule to prevent extrusion of the valve; and regulating the synovial fluid pressure within the capsule using the valve to drain synovial fluid and particulate debris from the capsule into surrounding tissue when a predetermined synovial fluid pressure is exceeded.

2. A method as recited in claim 1 wherein the valve includes a deflectable flap having a normally seated, closed position and said regulating step includes deflecting the flap from the seated position to an unseated, open position when the predetermined synovial fluid pressure is exceeded.

3. A method as recited in claim 1 wherein the valve includes a tubular housing having an external flange with holes therein and said step of securing the valve to the capsule includes passing suture material through the holes formed in the flange and the capsule.

4. A method as recited in claim 1 and further comprising, prior to said step of creating an opening in the capsule, the step of performing joint replacement surgery.

5. A method as recited in claim 1 and further comprising, prior to said step of creating an opening in the capsule, the step of approaching the capsule arthroscopically.

* * * * *